(12) United States Patent
Phillips

(10) Patent No.: US 8,475,849 B2
(45) Date of Patent: *Jul. 2, 2013

(54) FORMULATIONS AND TREATMENTS FOR WELL-BEING

(75) Inventor: Jon Phillips, Noosa Heads (AU)

(73) Assignee: Dolphst Pty Ltd., Queensland (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/082,579

(22) Filed: Apr. 8, 2011

(65) Prior Publication Data

US 2011/0182885 A1 Jul. 28, 2011

Related U.S. Application Data

(63) Continuation of application No. 11/793,987, filed as application No. PCT/AU2005/001966 on Dec. 23, 2005, now Pat. No. 7,927,631.

(30) Foreign Application Priority Data

Dec. 24, 2004 (AU) .............................. 2004907339
Jul. 21, 2005 (AU) .............................. 2005903864

(51) Int. Cl.
*A61K 36/00* (2006.01)
*A61K 36/704* (2006.01)
*A61K 36/258* (2006.01)

(52) U.S. Cl.
USPC ......... 424/725; 424/157.1; 424/752; 424/728

(58) Field of Classification Search
None
See application file for complete search history.

(56) References Cited

U.S. PATENT DOCUMENTS

| | | | |
|---|---|---|---|
| 5,904,924 A | 5/1999 | Gaynor et al. | |
| 6,039,950 A | 3/2000 | Khwaja et al. | |
| 2002/0119928 A1 | 8/2002 | McAnalley | |
| 2002/0150547 A1* | 10/2002 | Lee et al. | 424/74 |
| 2003/0028169 A1* | 2/2003 | Fossel | 604/500 |
| 2003/0198685 A1 | 10/2003 | Yegorova | |
| 2004/0126440 A1 | 7/2004 | Frager et al. | |
| 2004/0197430 A1 | 10/2004 | Meyrowitz | |
| 2004/0213859 A1* | 10/2004 | Zelickson | 424/725 |
| 2004/0237663 A1 | 12/2004 | Farber et al. | |
| 2004/0241260 A1 | 12/2004 | Senin et al. | |
| 2005/0250746 A1 | 11/2005 | Iammatteo | |

FOREIGN PATENT DOCUMENTS

| | | |
|---|---|---|
| CN | 1336120 | 2/2002 |
| GB | 2240715 | 8/1991 |
| JP | 1261322 | 10/1989 |
| JP | 02006403 A * | 1/1990 |
| JP | 8073369 | 3/1996 |
| JP | 2000001432 | 1/2000 |
| JP | 2003169632 | 6/2003 |
| KR | 20010088727 | 9/2001 |
| KR | 20040007174 | 1/2004 |
| WO | WO 94/05250 * | 3/1996 |
| WO | WO9702831 | 1/1997 |
| WO | WO 98/36759 * | 8/1998 |
| WO | WO9921009 | 4/1999 |
| WO | WO9956758 | 11/1999 |
| WO | WO0247493 | 6/2002 |
| WO | WO0247612 | 6/2002 |
| WO | WO02067960 | 9/2002 |
| WO | WO02067961 | 9/2002 |
| WO | WO02102163 | 12/2002 |
| WO | WO03009741 | 2/2003 |
| WO | WO03021515 | 3/2003 |
| WO | WO2006066323 | 6/2006 |
| WO | WO2006073457 | 7/2006 |
| ZA | 9904696 | 1/2000 |

OTHER PUBLICATIONS

Lowe et al, Zinc source influences zinc retention in hair and hair growth in the dog, Journal of Nutrition (1994), 124(12S), 2575S-6S.*
Kaplan, Steven A.; "5α-Reductase inhibitors: What role should they play?" Urology. 2001, 58(6A): 65-70.
"Methylsulfonylmethane (MSM)"; Alternative Medicine Review. 2003, 8(4): 438-441.
Do Monte Fabricio Hoffmann Martins et al.; "Antinociceptive and anti-inflammatory properties of the hydroalcoholic extract of stems from *Equisetum arvense* L. in mice"; Pharmacological Research (2004), 49(3): 239-243.
Oh H et al "Hepatoprotective and free radical scavenging activities of phenolic petrosins and flavonoids isolated from *Equisetum arvense*"; Journal of Ethnopharmacology (2004), 95(2-3): 421-42.
Li Jiping et al,; "Panax quinquefolium saponins protects low density lipoproteins from oxidation"; Life Sciences (1999), 64(1): 53-62.
Yang et al.; "Protective effects of Panax quinquefolium saponin on oxidative damage of cultured rat cardiac cells"; China Journal of Chinese Materia Medica (1992), 17(9):555-7.

* cited by examiner

*Primary Examiner* — Qiuwen Mi
(74) *Attorney, Agent, or Firm* — Abelman, Frayne & Schwab

(57) ABSTRACT

A formulation for well-being in humans including: extracts from the herbal varieties, *Polygonum multiflorum, Panax quinquefolium, Gingko biloba*, and *Equisetum arvense*; beta sitosterol methyl sulfonyl methane; soy isoflavones; levo-arginine; inositol; niacin; pantothenic acid or salts thereof; alpha-tocopherol; biotin; pyridoxine hydrochloride zinc (or amino acid chelate thereof); and colostrum.

2 Claims, No Drawings

FORMULATIONS AND TREATMENTS FOR WELL-BEING

CROSS-REFERENCE TO RELATED APPLICATIONS

This application is continuation of U.S. application Ser. No. 11/793,987, issued as U. S. Pat. No. 7,927,631 filed Jun. 22, 2009, which is a National Phase of PCT/AU2005/001966, filed 23 Dec. 2005, which claims priority from Australian Application Nos. 2004907339, filed 24 Dec. 2004 and 2005903864, filed 21 Jul. 2005, all of which are incorporated herein by reference.

FIELD OF INVENTION

THIS INVENTION relates to formulations and treatments for well-being. The invention is primarily directed to formulations and treatments for human health and well-being, but may be used in respect of unrelated conditions, such as alopecia.

BACKGROUND ART

Herbal extracts and formulations have long been used and/ or suggested for well-being in humans. Efficacy varies for such extracts and formulations. Generally, such treatments are either topical or systemic, but sometimes can be both. In the art, the term "well-being" is used to refer to a person's general health, particularly physical health, and well-being. In more recent times, the term "wellness" has been coined, though no particular connotational boundaries are strictly applied to any of these terms. In this specification, the term "well-being" is used in an encompassing sense to embrace such concepts including those described above unless the context requires otherwise.

The present invention aims to provide formulations and treatments for well-being in humans which alleviate one or more of the shortcomings of the prior art. Other aims and advantages of the invention may become apparent from the following description.

DISCLOSURE OF THE INVENTION

With the foregoing in view, this invention in a first aspect resides broadly in a formulation for well-being in humans including:
  extracts from the herbal varieties:
  Polygonum multiflorum,
  Panax quinquefolium,
  Gingko biloba, and
  Equisetum arvense;
  beta sitosterol
  methyl sulfonyl methane;
  soy isoflavones;
  levo-arginine;
  inositol;
  niacin;
  pantothenic acid or salts thereof;
  alpha-tocopherol;
  biotin;
  pyridoxine hydrochloride
  zinc (or amino acid chelate thereof); and
  colostrum.

In a second aspect, the present invention resides broadly in a formulation for well-being in humans including a 5-alpha reductase production inhibitor and methylsulfonylmethane.

Preferably, the 5-alpha reductase production inhibitor is selected from one or more phytosterols, particularly, as equivalents to beta-sitosterol. Alternatively, or in addition thereto, the 5-alpha reductase production may inhibitor may include extract from *Serenoa repens*, or Saw palmetto. The herbal extracts may also include *Pygeum repens*. The formulation may also include thiamin. The formulation may also include riboflavin.

In a third aspect, the present invention resides broadly in a formulation for well-being in humans including:
  a 5-alpha reductase production inhibitor;
  methylsulfonylmethane; and
  extract from the herbal variety *Polygonum multiflorum*.

In a fourth aspect, the present invention resides broadly in the present invention resides broadly in a formulation for well-being in humans including:
  a 5-alpha reductase production inhibitor;
  methylsulfonylmethane;
  extract from the herbal variety *Polygonum multiflorum*; and
  colostrum.

In a fifth aspect, the present invention resides broadly in the present invention resides broadly in a formulation for well-being in humans including:
  a 5-alpha reductase production inhibitor;
  methylsulfonylmethane;
  extract from the herbal variety *Polygonum multiflorum*; and
  levo-arginine.

In a sixth aspect, the present invention resides broadly in the present invention resides broadly in a formulation for well-being in humans including:
  a 5-alpha reductase production inhibitor;
  methylsulfonylmethane;
  extract from the herbal variety *Polygonum multiflorum*;
  levo-arginine and
  colostrum.

In a seventh aspect, the present invention resides broadly in the present invention resides broadly in a formulation for well-being in humans including:
  a 5-alpha reductase production inhibitor;
  methylsulfonylmethane;
  extract from the herbal variety *Polygonum multiflorum*;
  levo-arginine;
  colostrum; and
  *Gingko biloba*.

In an eighth aspect, the present invention resides broadly in a formulation for well-being in humans including:
  extract from the herbal variety *Polygonum multiflorum*;
  a 5-alpha reductase production inhibitor;
  methylsulfonylmethane; and
  colostrum.

Preferably, the formulation includes zinc amino acid chelate. Preferably the formulation includes *Gingko biloba*. More preferably, the formulation includes both zinc amino acid chelate and *Gingko biloba*. It is further preferred that the formulation includes any one or more extracts from the herbal varieties:
  *Polygonum multiflorum;*
  *Gingko biloba;*
  *Equisetum arvense;*
  *Panax quinquefolium.*

It is further preferred that the formulation includes any one or more of the following components:
  one or more soy isoflavones;
  levo-arginine;
  inositol;

niacin;
biotin;
calcium pantothenate;
dextro-alpha-tocopherol;
pyridoxine hydrochloride.

Preferably, the colostrum is bovine colostrum. However, it will be appreciated that other mammalian sources of colostrum may be used, particularly colostrum which are efficacious in ameliorating the reduction of growth hormone ("GH") and/or insulin-like growth factor 1 ("IGF-1") with ageing. Preferably, the components are provided in relative quantities selected to provide efficacy in respect of their known functional qualities.

In a ninth aspect, the present invention resides broadly in a formulation for well-being in humans including, in a dosage in the range of 3 g to 8 g:
phytosterols in the range of 200 mg to 2500 mg;
the quantitative equivalent of *Polygonum multiflorum* root 4:1 in 70% EW in the range of 600 mg to 2600 mg;
methylsulfonylmethane in the range of 500 mg to 2000 mg; and
bovine colostrum in the range of 500 mg to 2000 mg.

Preferably, the formulation further includes the quantitative equivalent of *Gingko biloba* leaf extract 50:1 in 70% EW in the range of 50 mg to 1000 mg. Preferably, the formulation further includes the quantitative equivalent of zinc amino acid chelate 20% in the range of 10 mg to 40 mg. More preferably, the formulation includes both the *Gingko biloba* and the zinc amino acid chelate. It is also preferred that the formulation includes any one or more of the following components:
arginine in the range of 120 mg to 500 mg;
biotin in the range of 0.7 mg to 5 mg;
nicotinic acid in the range of 5 mg to 30 mg;
calcium pantothenate in the range of 10 mg to 400 mg;
pyridoxine hydrochloride in the range of 10 mg to 400 mg;
d-α-tocopherol acetate in the range of 200 IU to 800 IU; and
colloidal anhydrous silica in the range of 60 mg to 500 mg.

It is also preferred that the formulation also include any one or more of the following components:
the quantitative equivalent of *Glycine Max* (soy) seed 65:1 in 75% EW in the range of 80 mg to 3250 mg;
the quantitative equivalent of *Panax quinquefolium* root extract 3:1 in 15% EW in the range of 50 mg to 1000 mg;
the quantitative equivalent of *Equisetum arvense* herb extract 4:1 in 100% water in the range of 50 mg to 1000 mg;
inositol in the range of 70 mg to 300 mg;

Preferably, the phytosterols are in the range of 200 mg to 2500 mg. More preferably, the phytosterols are in the range of 200 mg to 1000 mg. Preferably, the *Gingko biloba* extract is in the range of 50 mg to 1000 mg. More preferably, the *Gingko biloba* extract is in the range of 50 mg to 500 mg. Preferably, the *Panax quinquefolium* root extract is in the range of 50 mg to 1000 mg. More preferably, the *Panax quinquefolium* root extract is in the range of 50 mg to 500 mg. Preferably, the *Equisetum arvense* herb extract is in the range of 50 mg to 1000 mg. More preferably, the *Equisetum arvense* herb extract is in the range of 50 mg to 500 mg. Preferably, the bovine colostrum is in the range of 50 mg to 2000 mg. More preferably, the bovine colostrum is in the range of 500 mg to 1000 mg. Preferably, the biotin is in the range of 0.7 mg to 3 mg. Preferably, the pyridoxine hydrochloride is in the range of 100 mg to 400 mg. Trusil natural lemon/lime in the range of 6 to 26 mg or a flavouring agent equivalent thereto may also be added to the formulation. Fructose in the range of 125 mg to 500 mg or a sweetening agent equivalent thereto may also be added to the formulation.

In a tenth aspect, the present invention resides broadly in a formulation for well-being of a human patient including:
a biological sulfur nutritional supplement for providing biologically active sulfur;
one or more dihydrotestosterone blocking components for inhibiting the binding of dihydrotestosterone to receptor sites and/or inhibits the action of 5-alpha-reductase in converting testosterone to dihydrotestosterone;
one or more capillary blood-flow promoters for promoting capillary blood flow;
a growth factor component for promoting cell growth by ameliorating the reduction of growth hormone ("GH") and/or insulin-like growth factor 1 ("IGF-1") with ageing;
an amino acid component having at least some of all of the essential amino acids for human metabolism; and
a mineral component for introducing at least the minerals silicon and zinc into the patient.

Preferably, the formulation includes a vitamin component having at least some vitamin B1, vitamin B2, vitamin B3, vitamin B5, vitamin B8, vitamin $B_x$, and vitamin E.

Preferably, the components are selected from the phytosterols, *Polygonum multiflorum* root (fo-ti), *Glycine Max* (soy) seed, *Gingko biloba* leaf, *Panax quinquefolium* root, *Equisetum arvense*, inositol, methylsulfonylmethane, bovine colostrum, arginine, biotin, nicotinic acid, calcium pantothenate, pyridoxine hydrochloride, d-α-tocopherol acetate, Trusil natural lemon/lime or a flavouring agent equivalent thereto, fructose or a sweetening agent equivalent thereto, colloidal anhydrous silica and zinc amino acid chelate to make up a dosage in the range of 3 g to 8 g as set forth in the ninth aspect of the invention described herein.

Preferably, at least one of the capillary blood-flow promoters is functional in use to promote opening of potassium channels in cell membranes of patients. Preferably, the amino acid component includes isoflavones and/or phytosterols. More preferably, the amino acid component includes a phytoestrogen. More preferably, the amino acid component includes Genistein. In another preferred form, the amino acid component includes Daidzien. The vitamin and mineral components may be constituted from one or more sources. For example, the silicon mineral may be derived from the herb known as horsetail, *Equisetum arvense*. The zinc mineral may be contained in a zinc citrate or the like.

Preferably, preparation of the formulation for ingestion includes forming the components into respective component powders, mixing the component powders together and packaging the powder into predetermined dosage packs. One preferred dosage pack contains the mixed powder in the range of 3 g to 9 g powder. In a particular preferred form, the dosage is 5.5 g powder. In such form, it is preferred that the mixed powder be ingested in a drink, such as water, but it will be appreciated that a wide range of potable liquids would be suitable. It is suggested that a monthly supply of 200 g to 1000 g powder is efficacious when taken in accordance with the method of the invention. Of course, colouring and/or flavouring additives may be included, as well as dispersing and/or emulsifying agents, thickeners, preservatives or the like.

The powder may be formed so as to have different flavourings and/or colourings. Moreover, the powder may be flavoured differently for different diluents, such as, for example, a fruit-type flavour for mixing in water and a vanilla, chocolate or caramel flavour for mixing in milk or non-dairy equivalents of milk.

In an eleventh aspect, the present invention resides broadly in a medicinal formulation for well-being in humans including:

extracts from the herbal varieties:
Polygonum multiflorum;
Gingko biloba;
Equisetum arvense;
Panax quinquefolium;
methylsulfonylmethane;
levo-arginine;
a 5-alpha reductase production inhibitor;
one or more soy isoflavones;
inositol;
niacin;
biotin;
calcium pantothenate;
dextro-alpha-tocopherol;
pyridoxine hydrochloride;
zinc amino acid chelate; and
colostrum.

The constituents of the medicinal formulation are preferably selected substantially in accordance with the limitations of corresponding constituents of the other corresponding aspects of the invention as herein described.

Preferably, the colostrum is bovine colostrum. However, it will be appreciated that other mammalian sources of colostrum may be used, particularly colostrum which is efficacious in ameliorating the reduction of growth hormone ("GH") and/or insulin-like growth factor 1 ("IGF-1") with ageing. Preferably, the components are provided in relative quantities selected to provide efficacy in respect of their known functional qualities.

In a twelfth aspect, the present invention resides broadly in a formulation for well-being of a patient including, in a dosage in the range of 3 g to 8 g:
phytosterols in the range of 200 mg to 2500 mg;
the quantitative equivalent of Polygonum multiflorum root 4:1 in 70% EW in the range of 600 mg to 2600 mg;
the quantitative equivalent of Glycine Max (soy) seed 65:1 in 75% EW in the range of 800 mg to 3250 mg;
the quantitative equivalent of Gingko biloba leaf extract 50:1 in 70% EW in the range of 50 mg to 1000 mg;
the quantitative equivalent of Panax quinquefolium root extract 3:1 in 15% EW in the range of 50 mg to 1000 mg;
the quantitative equivalent of Equisetum arvense herb extract 4:1 in 100% water in the range of 50 mg to 1000 mg;
inositol in the range of 70 mg to 300 mg;
methylsulfonylmethane in the range of 500 mg to 2000 mg;
bovine colostrum in the range of 500 mg to 2000 mg;
arginine in the range of 120 mg to 500 mg;
biotin in the range of 0.7 mg to 5 mg;
nicotinic acid in the range of 5 mg to 30 mg;
calcium pantothenate in the range of 100 mg to 400 mg;
pyridoxine hydrochloride in the range of 10 mg to 400 mg;
d-α-tocopherol acetate in the range of 200 IU to 800 IU;
Trusil natural lemon/lime in the range of 6 to 26 mg or a flavouring agent equivalent thereto;
fructose in the range of 125 mg to 500 mg or a sweetening agent equivalent thereto;
colloidal anhydrous silica in the range of 60 mg to 500 mg; and
the quantitative equivalent of zinc amino acid chelate 20% in the range of 10 mg to 40 mg.

It will be appreciated that the sweetening and flavouring agents are not essential to the efficacy of the formulation.

In a thirteenth aspect, the present invention resides broadly in a method of enhancing the well-being of a human patient including the steps of:
preparing a predetermined quantity of a formulation consisting of: extracts from the herbal varieties Polygonum multiflorum, Panax quinquefolium, Gingko biloba, and Equisetum arvense; beta sitosterol; methyl sulfonyl methane; soy isoflavones; levo-arginine; inositol; niacin; pantothenic acid or salts thereof; alpha-tocopherol; biotin; pyridoxine hydrochloride; zinc (or amino acid chelate thereof); and colostrum and
preparing the quantity for ingestion by the human patient.

In a fourteenth aspect, the present invention resides broadly in a method of enhancing the well-being of a human patient including the steps of:
preparing a predetermined quantity of a formulation consisting of: a biological sulfur nutritional supplement for providing biologically active sulfur; one or more capillary blood-flow promoters for promoting capillary blood flow; a growth factor component for promoting cell growth by ameliorating the reduction of growth hormone ("GH") and/or insulin-like growth factor 1 ("IGF-1") with ageing; an amino acid component having at least some of all of the essential amino acids for human metabolism; a mineral component for introducing at least the minerals silicon and zinc into the patient; and a vitamin component having at least some vitamin B1, vitamin B2, vitamin B3, vitamin B5, vitamin B8, vitamin $B_x$, and vitamin E; and
preparing the predetermined quantity for ingestion by the human patient.

While the formulation has been found to have increased efficacy when used with a systemic mode of delivery, it will be appreciated that the method of the invention is not limited thereto.

Preferably, at least one of the capillary blood-flow promoters is functional in use to promote opening of potassium channels in cell membranes of patients. Preferably, the amino acid component includes isoflavones and/or phytosterols. More preferably, the amino acid component includes a phytoestrogen. More preferably, the amino acid component includes Genistein. In another preferred form, the amino acid component includes Daidzien. The vitamin and mineral components may be constituted from one or more sources. For example, the silicon mineral may be derived from the herb known as horsetail, Equisetum arvense. The zinc mineral may be contained in a zinc citrate or the like.

Preferably, preparation of the formulation for ingestion includes forming the components into respective component powders, mixing the component powders together and packaging the powder into predetermined dosage packs. One preferred dosage pack contains the mixed powder in the range of 2 g to 10 g powder. In a particular preferred form, the dosage is 5.5 g powder. Another preferred dosage pack contains one week's or one month's or part thereof supply of powder to be ingested in the range of quantity detailed above taken twice daily. In such form, it is preferred that the mixed powder be ingested in a drink, such as water, but it will be appreciated that a wide range of potable liquids would be suitable. Of course, colouring and/or flavouring additives may be included, as will as dispersing and/or emulsifying agents, thickeners, preservatives or the like.

BRIEF DESCRIPTION OF THE EXAMPLES

In order that the invention may be more readily understood and put into practical effect, reference will now be made to one or more examples of the invention wherein at least some of the aspects and embodiments of the invention are described from experimental work in the development of the invention.

DETAILED DESCRIPTION OF THE EXAMPLES

Example 1

A batch of material was formulated according to the details set forth in Table 1 below.

| Ingredient (and strength) | Label Claim | mg | mg/dose | overage | mg per g (including overage) | weight for mix (kg) |
|---|---|---|---|---|---|---|
| phytosterols (equiv. B-sitosterol 33%) | 500.00 | 303 | 1515 | 3% | 312.09 | 35.344 |
| *Polygonum multiflorum* (fo ti) root 4:1 in 70% EW | 1350.00 | 67.5 | 337.5 | 5% | 70.88 | 8.027 |
| *Glycine max* (soy) seed 65:1 in 75% EW | 1625.00 | 5 | 25 | 0% | 5.00 | 0.566 |
| *Gingko biloba* leaf ext (50:1 in 70% EW) | 100.00 | 0.4 | 2 | 5% | 0.42 | 0.048 |
| *Panax quinquefolium* root ext (3:1 in 15% EW) | 100.05 | 6.67 | 33.35 | 5% | 7.00 | 0.793 |
| *Equisetum arvense* herb ext (horsetail) (4:1 in 100% water) | 100.00 | 5 | 25 | 5% | 5.25 | 0.595 |
| inositol | 150.00 | 30 | 150 | 5% | 31.50 | 3.567 |
| methylsulfonylmethane (MSM) | 1000.00 | 200 | 1000 | 5% | 210.00 | 23.783 |
| colostrum (bovine) | 1000.00 | 200 | 1000 | 5% | 310.00 | 23.783 |
| arginine | 250.00 | 50 | 250 | 0% | 50.00 | 5.663 |
| biotin | 1.40 | 0.28 | 1.4 | 5% | 0.29 | 0.033 |
| nicotinic acid | 15.00 | 3 | 15 | 5% | 3.15 | 0.357 |
| calcium pantothenate | 200.00 | 40 | 200 | 4% | 41.67 | 4.719 |
| pyridoxine hydrochloride | 25 | 5 | 25 | 5% | 5.24 | 0.595 |
| d-α-tocopherol acetate (dry vitamin E acetate) | 400 IU | 107.2 | 536 | 5% | 112.56 | 12.747 |
| Trusil natural lemon/lime | 13 | 2.6 | 13 | 5% | 2.73 | 0.309 |
| fructose | 250 | 50 | 250 | 0% | 50.00 | 5.663 |
| silica colloidal anhydrous | 125 | 25 | 125 | 0% | 25.00 | 2.831 |
| zinc amino acid chelate 20% | 20 | 20 | 100 | 5% | 21.00 | 2.378 |
| Total | 6804.45 | 1120.65 | 5603.25 | | | 131.799 |

The resulting formulation was tested against a placebo on a number of individuals for well-being. The test results revealed that the formulation was efficacious in promoting well-being.

Example 2

A batch of material was formulated according to the details set forth in Table below.

| INGREDIENT | LABEL CLAIM (mg per 5 g serve) | Mg | Mg/Dose |
|---|---|---|---|
| Phytosterols (Equiv B-sitosterol 33%) | 125.00 | 75.75 | 378.75 |
| *Polygonum multiflorum* (Fo Ti) root 4:1 in 70% EW | 337.50 | 16.88 | 84.38 |
| *Glycine Max* (Soy) seed 65:1 in 75% EW | 406.25 | 1.25 | 6.25 |
| *Ginkgo Biloba* leaf ext (50:1 in 70% EW) | 25.00 | 0.10 | 0.50 |
| *Panax quinquefolium* root ext (3:1 in 15% EW) | 25.01 | 1.67 | 8.34 |
| *Equisetum arvense* herb Ext (Horsetail) (4:1 in 100% Water) | 25.00 | 1.25 | 6.25 |
| Inositol | 37.50 | 7.50 | 37.50 |
| Methylsulfonylmethane (MSM) | 250.00 | 50.00 | 250.00 |
| Colostrum (Bovine) | 250.00 | 50.00 | 250.00 |
| Arginine | 62.50 | 12.50 | 62.50 |
| Biotin | 0.35 | 0.07 | 0.35 |
| Nicotinic Acid | 3.75 | 0.75 | 3.75 |

-continued

| INGREDIENT | LABEL CLAIM (mg per 5 g serve) | Mg | Mg/Dose |
|---|---|---|---|
| Calcium Pantothenate | 50.00 | 10.00 | 50.00 |
| pyridoxine Hydrochloride | 6.25 | 1.25 | 6.25 |
| d-alpha tocopheryl acetate (Dry Vitamin E Acetate) | 100 IU | 26.80 | 134.00 |
| Trusil Natural Lemon/Lime | 3.25 | 0.65 | 3.25 |
| Fructose | 62.50 | 12.50 | 62.50 |
| Silica - Colloidal Anyhydrous | 31.25 | 6.25 | 31.25 |
| Zinc Amino Acid Chelate 20% | 5.00 | 5.00 | 25.00 |
| Total | 1706.11 | 280.16 | 1400.81 |

The resulting formulation was tested against a placebo on a number of individuals for well-being. The test results revealed that the formulation was efficacious in promoting well-being.

Example 3

A batch of material was formulated according to the details set forth in Table 3 below.

| INGREDIENT | LABEL CLAIM (mg per 5 g serve) | Mg | Mg/Dose |
|---|---|---|---|
| Phytosterols (Equiv B-sitosterol 33%) | 250.00 | 151.50 | 757.50 |
| *Polygonum multiflorum* (Fo Ti) root 4:1 in 70% EW | 675.00 | 33.75 | 168.75 |
| *Glycine Max* (Soy) seed 65:1 in 75% EW | 812.50 | 2.50 | 12.50 |
| *Ginkgo Biloba* leaf ext (50:1 in 70% EW) | 50.00 | 0.20 | 1.00 |
| *Panax quinquefolium* root ext (3:1 in 15% EW) | 50.03 | 3.34 | 16.68 |
| *Equisetum arvense* herb Ext (Horsetail) (4:1 in 100% Water) | 50.00 | 2.50 | 12.50 |
| Inositol | 75.00 | 15.00 | 75.00 |
| Methylsulfonylmethane (MSM) | 500.00 | 100.00 | 500.00 |
| Colostrum (Bovine) | 500.00 | 100.00 | 500.00 |
| Arginine | 125.00 | 25.00 | 125.00 |
| Biotin | 0.70 | 0.14 | 0.70 |
| Nicotinic Acid | 7.50 | 1.50 | 7.50 |
| Calcium Pantothenate | 100.00 | 20.00 | 100.00 |
| pyridoxine Hydrochloride | 12.50 | 2.50 | 12.50 |
| d-alpha tocopheryl acetate (Dry Vitamin E Acetate) | 200 IU | 53.60 | 268.00 |
| Trusil Natural Lemon/Lime | 6.50 | 1.30 | 6.50 |
| Fructose | 125.00 | 25.00 | 125.00 |
| Silica - Colloidal Anyhydrous | 62.50 | 12.50 | 62.50 |
| Zinc Amino Acid Chelate 20% | 10.00 | 10.00 | 50.00 |
| Total | 3412.23 | 560.33 | 2801.63 |

The resulting formulation was tested against a placebo on a number of individuals for well-being. The test results revealed that the formulation was efficacious in promoting well-being.

Example 4

A batch of material was formulated according to the details set forth in Table 4 below.

| INGREDIENT | LABEL CLAIM (mg per 5 g serve) | Mg | Mg/Dose |
|---|---|---|---|
| Phytosterols (Equiv B-sitosterol 33%) | 1000.00 | 606.00 | 3030.00 |
| *Polygonum multiflorum* (Fo Ti) root 4:1 in 70% EW | 2700.00 | 135.00 | 675.00 |
| *Glcine Max* (Soy) seed 65:1 in 75% EW | 3250.00 | 10.00 | 50.00 |
| *Ginkgo Biloba* leaf ext (50:1 in 70% EW) | 200.00 | 0.80 | 4.00 |

-continued

| INGREDIENT | LABEL CLAIM (mg per 5 g serve) | Mg | Mg/Dose |
|---|---|---|---|
| *Panax quinquefolium* root ext (3:1 in 15% EW) | 200.10 | 13.34 | 66.70 |
| *Equisetum arvense* herb Ext (Horsetail) (4:1 in 100% Water) | 200.00 | 10.00 | 50.00 |
| Inositol | 300.00 | 60.00 | 300.00 |
| Methylsulfonylmethane (MSM) | 2000.00 | 400.00 | 2000.00 |
| Colostrum (Bovine) | 2000.00 | 400.00 | 2000.00 |
| Arginine | 500.00 | 100.00 | 500.00 |
| Biotin | 2.80 | 0.56 | 2.80 |
| Nicotinic Acid | 30.00 | 6.00 | 30.00 |
| Calcium Pantothenate | 400.00 | 80.00 | 400.00 |
| pyridoxine Hydrochloride | 50.00 | 10.00 | 50.00 |
| d-alpha tocopheryl acetate (Dry Vitamin E Acetate) | 800 IU | 214.40 | 1072.00 |
| Trusil Natural Lemon/Lime | 26.00 | 5.20 | 26.00 |
| Fructose | 500.00 | 100.00 | 500.00 |
| Silica - Colloidal Anyhydrous | 250.00 | 50.00 | 250.00 |
| Zinc Amino Acid Chelate 20% | 40.00 | 40.00 | 200.00 |
| Total | 13648.90 | 2241.30 | 11206.50 |

The resulting formulation was tested against a placebo on a number of individuals for well-being. The test results revealed that the formulation was efficacious in promoting well-being.

In use, the formulations and methods of the present invention may be used for increasing "wellness" or well being in a human patient. It is believed that the formulations of the present invention contribute synergistically to provide enhanced results of greater efficacy than either the individual components or modes of treatment. The beneficial effects of the treatment are believed to include remediation of incorrect flow or lack of circulation both peripheral and cardiovascular, and/or incorrect hormonal or dietary balance.

The *Polygonum multiflorum* (fo-ti) root extract component may also be known as "He Shou Wu". Fo-ti root is thought to be a tonic for the endocrine glands, liver and kidneys. Fo-ti-root contains many vitamins and minerals that are vital for hair, including the B-complex vitamins, vitamin C, silicon, zinc and vitamin A. It has been used in China specifically as a restorative tonic and for promoting longevity. Traditional Chinese medicine records it as a "Qi tonic"—that is, a herb that benefits the immune system and has hormonal effects. It is a traditional treatment for poor sleep. The herb is regarded as a slow-acting sedative, the benefits of which are felt over a period of months. Clinical observation of its use indicates increased mental clarity, relief of insomnia, vertigo and constipation, and as a blood, liver and kidney restorative, generally for longevity and sexual function. Recent evidence shows it to be effective against high blood pressure and hardening of the arteries and veins.

Insofar as colostrum in concerned, it is a material produced by nearly all mammals, by the mother of the offspring soon after birth. Medical research has shown that the most important immune and growth factors for human adults, children and animals can be provided by bovine colostrum. Because colostrum is a food rather than a drug it is free of toxicity and can be consumed without any known side effects. Colostrum research conducted by major medical centres and universities has shown clinically active bovine supplements derived from dairy cows naturally stimulates the nutrient-rich properties that a mother produces for her new-born offspring just after birth. Colostrum provides a supercharged blend of vital proteins, antibodies, anti-oxidants, immunoglobulin, growth factors, vitamins, minerals, enzymes and amino acids. The highly charged nature of colostrum precludes it being produced at sustained levels throughout the lactation of a mammalian parent. However, its initial production soon after parturition is provided by nature to give an early boost to the new born mammalian offspring. Colostrum is also believed to have the functional quality of combatting and even reversing signs of aging.

According to Dr Rona Zoltan, colostrum may well be nature's most practical protection against infection. It is completely natural, free of side effects and an excellent alternative to hundreds of drugs. Bovine colostrum has been used in India for thousands of years by Ayurvedic physicians documenting the physical benefits of colostrum and its healing and therapeutic abilities. Mammals produce colostrum shortly after parturition as a powerful, nutrient-rich fluid. It provides a multi-charged blend of vital proteins, antibodies, antioxidants, immunoglobulins, growth factors, vitamins, minerals, enzymes and amino acids. Colostrum is the primary life sustaining food—bovine colostrum has over thirty-seven immune factors when properly processed, as well as eight growth factors.

Methylsulfonylmethane is a natural source of sulfur in the metabolism. Sulfur is necessary for collagen formation, and is also required for many of the body's structural molecules. Among the many benefits are joint and tissue health, defence against allergies and asthma, nutritional support for healthy energy levels and toxin elimination. Methylsulfonylmethane has been called "nature's beauty mineral" because it is believed to keep the hair glossy and smooth, keeps the complexion clear and youthful, and is believed to contribute to the synthesis of collagen. This material is prevalent in keratin, a tough protein substance necessary for the health and maintenance for the hair, nails and skin, including defence against ageing. Some of the functional qualities of methylsufonylmethane include improved micro-circulation to the hair and scalp, maintaining structure of the proteins in the body, helping the formulation of keratin and aiding in the production of immunoglobulin. Keratin is essential for hair and nail growth and immunoglobulin maintains the immune system.

Beta sitosterol can be derived, for example, from Saw Palmetto (*Serenoa Repens*), a native American member of the palm family. Saw palmetto is a source of a class of complex, chiefly unsaturated, solid alcohols widely distributed in plant an animal tissue, known as sterols. More specifically, plants contain phytosterols, or plant based sterols. Sitosterols are sterols that are found in food (sito=food). Beta sitosterol is plant based fat that slows the production of 5-alpha reductase and the binding of dihydrotestosterone to androgen receptors.

Research has shown that dihyrdotestosterone is an undesirable derivative of the androgenic hormone testosterone. Dihydrotestosterone floods and eventually strangles hair follicles of genetically predisposed individuals. The key to anti-androgenic complex lies in blocking dihydrotestosterone at the follicle receptor site. Recent scrutiny of the material has revealed its health benefits such as, for example, in addition to boosting the immune system, it enhances lymphocyte proliferation and NK-cell activity and NL-cell activity. This is believed to be particularly useful to people who are physically stressed, medically unwell or recovering from illness. Beta sitosterol is also been shown to reduce blood levels of cholesterol, provide prostate support, relieve inflammation, heal ulcers, enhance uterine tone, alleviate cramps, as well as provide an anti-viral, antibiotic and/or antimycotic agent.

It is believed that beta sitosterol is a multi-site inhibitor of the formation and actions of dihydrotestosterone, inhibiting most of the binding of the dihydrotestosterone, to receptor sites, blocking the up take of dihydrotestosterone and inhibiting the action of 5-alpha-reductase, which converts testosterone to dihydrotestosterone.

*Ginkgo biloba* is a herbal extract with a long standing tradition for use in providing natural vascular benefits when ingested or applied topically. *Gingko biloba* has been shown to protect small blood vessels and micro capillaries against loss of tone and increase in fragility. The herb also has application in treating male and female pattern hair loss. *Gingko biloba* is beneficial and due to its functional quality of dilating blood vessels (particularly small blood vessels) and has particular ability to increase peripheral blood circulation, especially to the brain. *Gingko biloba* is believed to have beneficial effects in preventing many conditions throughout the entire body due to poor blood supply. *Gingko biloba* can also act as a powerful anti oxidant and may contribute to the oxidation of free radicals, which are believed to contribute to premature aging. Anti oxidants also protect the eyes, cardio-vascular system and central nervous systems. In traditional Chinese medicine, *Gingko biloba* has been used to improve the heart and circulation. The herb has been used for many centuries by the Chinese, and has become a conventional supplement in Europe, and more recently, in the United States.

L-arginine is an amino acid, one of the building blocks of protein. However, in the present application, L-arginine serves as a precursor in the body for the production of nitric oxide, believed to have a critical role in human metabolism, and believed to be produced by the linings of the blood vessels known as the vascular endothelium. Because nitric oxide lasts only for a few seconds once produced, its discovery was particularly illusive, but once found, researchers appreciated that this was probably the mysterious molecule that controlled blood vessel dilation. L-arginine is an essential amino acid and one of the most important supplements available to improve circulation and blood vessel health. It is believed that nitric oxide causes blood vessels to relax, opening them up and promoting easy blood flow. Nitric oxide is believed to be involved in opening potassium channels known as "K-Channels". L-arginine has been shown to promote natural growth hormone (GH) release from pituitary gland. GH has been shown to support a healthy lifestyle and may minimise a related decline. This material may also assist in kidney control of solubles in the body. The amino acid is also said to support healthy cholesterol balance, support immune function, to aid in liver detoxification, to be essential for muscle growth and tissue repair, assist in the body maintaining healthy blood pressure, minimise cardiovascular dysfunction and encourage healthy heart cells.

In so far as Soy isoflavones are concerned, soy and most soy based products are believed to be the only plant food that has all the essential amino acids required of the human body, making it a "complete protein source". Soy foods generally do not have any cholesterol and most are high in fibre. In addition, soy has many vitamins, minerals and phyto-chemical compounds (like isoflavones) that work together to create numerous health benefits. Soy isoflavones are plant substances which are believed to contribute to hormonal balance when included as a dietary supplement. Soy products also include phytosterols. Soy isoflavones and phytosterols are known to supply mild estrogenic effects. The soy isoflavones, rich in phyto-nutrients, help prevent medical conditions associated with aging and from the large body of research can have a positive effect on hair for woman as well as for men. Soy beans contain phyto-estrogens, genistein being one, which has been shown to have significant 5-alpha-reductase blocking activity, and androgen modulating activity. Another phyto-estrogen from soy beans, daidzien, also helps block the 5-alpha-reductase enzyme. It is believed that this material may also reduce the risk of heart disease. Soy bean products have been shown to lower LDL ("Bad") cholesterol, and significantly increase HDL ("good") cholesterol. These substances are also believed to play an important role in protecting and maintaining strong and healthy bones, and as a treatment for osteoporosis.

Silica (horsetail herb) is believed to be the best and most concentrated plant source of the mineral silica for its introduction into the food chain. Silica is an important component of hair, nail, skin, bones, ligaments and collagen and is an essential herb needed for the physical integrity of these structures. Silica enhances the absorption of all minerals in the body. It has the effect of strengthening hair follicles and stimulates and increases growth of hair. Silica tends to decline as humans age. This decline can be responsible for many complaints associated with aging, and conditions have been linked to silica such as dry hair, hair loss, dry skin, weak brittle hair and nails, nervousness, poor energy levels and the like. Weak bone structure silica maximises the absorption of calcium by the bones, may be strengthened and taking horsetail has been clinically shown to help fractured and broken bones heal more quickly. Grains and cereal produced by modern farming practices tend to be depleted of nutrients and silica. It is believed that very few foods have a high enough silica content to supply human dietary needs. Horsetail is rich in silicic acid and silicates which provide approximately 2-3% elemental silicone. The high concentration of silica in horsetail is highly absorbable and utilised to facilitate calcium absorption, thereby promoting hair and bone growth and collagen formation. The herb also contains potassium, aluminium, manganese, calcium and 15 types of bioflavonoids, also known as vitamin P. Horsetail also supports the skeletal system by assisting in strengthening bones and connective tissues. Silicic acid contained in horsetail is believed to help improve circulation and build the immune nervous systems. It is also noted for stimulating thyroid function and helps facilitate calcium in the body, as well as in the healing of broken bones, arthritis, kidney and urinary tract disorders and the like.

The nutrient inositol is believed to be essential for keratinocyte, a component in the cells which line the hair follicles. Inositol is an essential component of the vitamin B group and is often referred to as Vitamin B8. Inositol has an important part to play, not only being required for optimal general health, but also having specific functions in the body in which it assists. Examples of these functions include hair growth, calming effect, lowering cholesterol in association with lecithin. The levels of inositol in the body can be depleted by caffeine, sulfonamide and excess water. Inositol is found in lecithin, whole grains, citrus fruit, liver, brewers yeast, vegetables, black strap molasses, soy beans and the like. The B group vitamins are important factors for proper maintenance of the nervous system, proper functioning of the cell and its energy metabolism. Any kind of mental and physical stress, as well as poor eating habits, greatly increase the body's need for B group vitamins. Since B group vitamins are water soluble, they are not stored and since they are not produced by anabolism, must be supplied as the body needs them on a regular basis. Inositol, being highly hydroxylated (chemically, it is hexahydroxycyclohexane) is believed also to provide hydroxyl radicals. Inositol is believed to be essential for overall growth.

Zinc is an essential mineral for body metabolism and has a myriad of health benefits for the human body. Zinc is believed to stimulate the activity of approximately 100 enzymes, substances which promote biochemical reactions in the body. Zinc supports normal growth and a healthy immune system. The mineral also helps to protect cells against oxidative damage, safeguard red blood cell membranes against oxidative effects against of other minerals such as copper and iron, keeps cell membrane contents in place and selectively allows salts and other components to flow in and out of cells. Zinc is also present in the mammalian male reproductive fluids. Dietary zinc is sourced from such foods as beans, whole grains, shellfish, red meat, dark meat, poultry and the like.

*Panax quinquefolium* root extract is also known by some as ginseng, a traditional herbal remedy from Asia, and used extensively in Asian cultures. It has a myriad of health benefits, including helping the body to cope with stress, enhance feelings of calm and serenity, enhance energy, alertness reflexes and endurance, have a positive effect on the cardiovascular and central nervous systems, fortify both white cells and antibodies, enhancing their production in the bone marrow, shorten recovery time from illness or injury, alleviate some of the effects of ageing, relieve tiredness, and act as a safe long-term stimulant. Ginseng also has been used as a sexual stimulant for both men and women, alleviating impotence in men and levelling the female cycle in women.

Vitamin E has been shown to retard cellular aging due to oxidation, the effect of maintaining peripheral circulation, is one of the more important anti oxidants, the strong presence of vitamin E being linked to longevity, reducing the effects of oxidated stress, and is a vital part of the formula involved in retarding cellular aging. Vitamin E is a natural detoxifier of impurities within the metabolic system of the body. It increases blood circulation for healthy hair growth but, as it cant be stored in the body, deficiencies can occur without a person being aware of it. It is essential for the body growth of body tissue cells and blood vessels. Longer living humans have been found to have higher amounts of vitamin E in their brain tissues.

Each member of the B vitamin group has a unique structure and performs a unique function in the human body. Vitamins B1, B2, B3 and biotin participate in different aspects of energy production, vitamin B6 is essential for amino acid metabolism, and folic acid facilitates steps required for cell division. Each of these vitamins has many additional functions. Biotin is believed to increase elasticity of the hair's cortex preventing breakage and also thickens actual hair cuticle providing a fuller appearance and sounder result as a result of the increase diameter of the hair shaft. Biotin is sometimes referred to as Vitamin H, however it is generally accepted as being one of the B group vitamins. The vitamin promotes hair growth, protects against dryness, is involved in bio synthesis of unsaturated fats and is needed for energy metabolism. Folic acid is a water-soluble B-complex vitamin which assists with hair and tissue growth and cell functions. Para aminobenzoic acid (PABA) is one of the lesser known members of the B complex family referred to above as vitamin $B_x$. It has been shown to be an anti grey hair vitamin. The vitamin has been shown to restore normal hair colour. PABA is commonly used in sunscreens. In so far as the other vitamin B's are concerned, Vitamin B1 (thiamine) has a role in the development of blood cells and the maintenance of hair and scalp and muscle tissue. Vitamin B2 (riboflavin) is involved in energy metabolism, and supports vision, hair and skin health. Vitamin B3 (niacin) is essential for the metabolism of carbohydrates, fat and alcohol, it helps maintain skin health and support the nervous and digestive systems. Pantothenic acid is considered to be important to the health of the skin and scalp, is necessary for the well being of every body cell and neither carbohydrate nor fat can be changed into energy without it. This nutrient is obtained from liver, kidney, egg yolks, whole grains, milk and potatoes. The combined effects of the materials used to formulate the formulation of the present invention are believed to provide benefits in health and wellness of an individual as well as the trichological effects in stopping and preventing dihydrotestosterone, the cause of hair loss and hair thinning in men and woman, as well as other effects. It is believed that the natural properties of the formulation of the present invention provide a more effective, quicker and widespread result than juice known as noni juice made from Tahitian noni berry and other currently available health and wellness products.

It is believed that whilst the entire combination of ingredients as set forth in the preferred embodiments of the invention works synergistically to provide the optimum general health and wellness benefits, it will be appreciated that particular wellness benefits can be obtained by using less that the full complement of ingredients.

Although the invention has been described with reference to specific examples, it will be appreciated by persons skilled in the art that the invention may be embodied in other forms which are encompassed within the broad scope and ambit of the invention as defined by the following claims.

What is claimed is:

1. A method for enhancing well-being in an individual, the method comprising administering to the individual a formulation comprising:
   i) methylsulfonylmethane;
   ii) beta-sitosterol;
   iii) an extract from Polygonum multiflorum;
   iv) an extract from Ginkgo biloba;
   v) an extract from Equisetum arvense;
   vi an extract from Panax quinquefolium;
   vii) an isoflavone;
   viii) arginine;
   ix) vitamin B3;
   x) vitamin B5;
   xi) vitamin B6;
   xii) vitamin B7;
   xiii) vitamin B8;
   xiv) vitamin E;
   xv) zinc; and
   xvi) colostrum.

2. The method of claim 1, wherein enhancing well-being comprises at least one of
   remediating incorrect flow or lack of circulation;
   promoting capillary blood flow;
   promoting cell growth;
   improving metabolism;

correcting a hormonal imbalance; or correcting a dietary imbalance;
in the individual.

\* \* \* \* \*